United States Patent
Brendler et al.

(10) Patent No.: US 6,754,307 B2
(45) Date of Patent: Jun. 22, 2004

(54) METHOD AND DEVICE FOR X-RAY EXPOSURE CONTROL

(75) Inventors: Joachim Brendler, Hamburg (DE); Horst Allmendinger, Elmshorn (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 60 days.

(21) Appl. No.: 10/139,676

(22) Filed: May 6, 2002

(65) Prior Publication Data

US 2002/0191741 A1 Dec. 19, 2002

(30) Foreign Application Priority Data

May 7, 2001 (DE) .......................................... 101 22 041

(51) Int. Cl.[7] .............................................. H05G 1/44
(52) U.S. Cl. ......................................... 378/108; 378/97
(58) Field of Search ............................ 378/96, 97, 108, 378/98.7

(56) References Cited

U.S. PATENT DOCUMENTS 4,097,741 A 6/1978 Pfeiler et al.
4,119,856 A * 10/1978 Franke .................. 378/97
4,956,857 A 9/1990 Kurosaki

FOREIGN PATENT DOCUMENTS

EP 0 063 644 12/1981

* cited by examiner

Primary Examiner—Craig E Church
(74) Attorney, Agent, or Firm—Thomas M. Lundin

(57) ABSTRACT

The invention relates to a method for exposure control which is intended notably for dynamic X-ray examinations of an object involving a varying X-ray absorption as well as to an X-ray generator which includes an automatic exposure control unit for carrying out such a method. The method and the device are characterized notably in that an exposure kV start voltage and a maximum exposure time Tmax (for example, 100 ms) can be defined; in order to avoid motional unsharpness in the image, these variables may not be exceeded. At the beginning of an exposure, the X-ray absorption of the object is measured and within a very short period of time (from 1 ms to 2 ms) an operating range of the exposure controller is selected in that either the exposure is controlled in known manner by varying the exposure time while keeping the exposure kV start voltage constant or, in the case of a correspondingly higher absorption and/or a smaller maximum exposure time Tmax, in that the exposure is controlled by changing the exposure kV voltage at the maximum exposure time.

11 Claims, 2 Drawing Sheets

METHOD AND DEVICE FOR X-RAY EXPOSURE CONTROL

BACKGROUND

Figure 1:
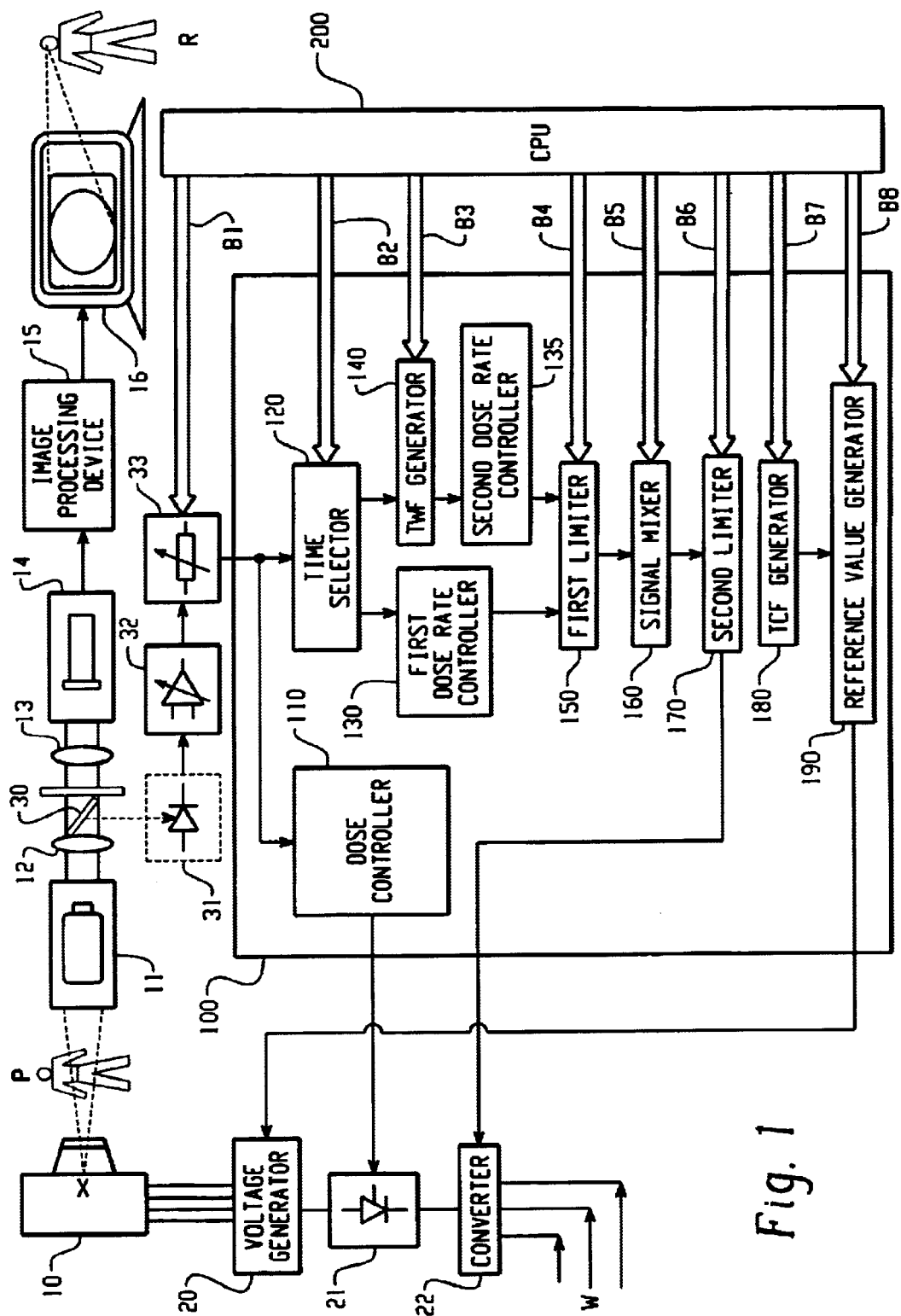

The invention relates to a method for X-ray exposure control, notably for exposures carried out during dynamic X-ray examinations of an object, that is, exposures during which the X-ray absorption of the object changes and/or the object moves. The invention also relates to an X-ray generator provided with an automatic exposure control device for carrying out such a method.

For X-ray examination of the human body and its organs it is necessary to carry out a large number of settings for an X-ray generator so as to achieve an optimum exposure of the examination zone. This is due to the fact that the density of the various organs or regions of the body is very different per se and also differs from one person to another, that is, in dependence on the size and the weight of the relevant person. In order to ensure a safe examination of the patient while applying an as small as possible radiation dose, furthermore, in practically all countries there are official regulations which allow given parameters to be adjusted or changed only within given limits.

Attention should be paid in particular to the following parameters which are dependent on one another, have to be adapted to one another and influence the acquired image each time in a different way.

On the one hand, the dose rate of the X-ray tube (that is, essentially the exposure kV voltage) determines the contrast and the contrast range of the objects imaged. The radiation dose, however, first of all determines the signal-to-noise ratio of the image whereas, in order to optimize the image sharpness notably in the case of moving objects, the exposure time may not exceed a given maximum value. Furthermore, for the adaptation or selection of these parameters it is also necessary to take into account the density (X-ray absorption) of the object to be examined, that is, generally speaking, the thickness of the patient. Finally, various legal rules and regulations apply also to the X-ray dose that is incident on a radiation receiver.

Various methods and devices are known for the partial automation of the adjustment of these parameters. For example, EP 0 073 644 describes a method in which, after preselection of given secondary conditions such as relative hardness number, exposure field format, film and foil sensitivity etc., first the X-ray exposure is carried out with a programmed tube voltage and a programmed tube current until a programmed dose is reached, and the time elapsing until that instant is measured. The X-ray exposure is then continued while using for the X-ray voltage and the mAs product a value which is associated with said measured time and is stored. The dose and/or the dose power of the X-rays is thus adapted to the density of the object to be imaged (object transparency).

This and other partly automated methods and devices whereby one of said parameters is determined in dependence on the other, preset or measured parameters, have the drawback that the image quality is dependent to a significant degree on the skills of the operator in suitably finding the relevant presetting. These methods and devices often reach their limits also in the case of dynamic processes where, for example exposures are to be performed with a moving contrast medium, because notably in cases where the dose rate is not optimally adjusted, a prolongation of the exposure time which is automatically imposed by a change of absorption may lead to lack of sharpness in the image.

SUMMARY

Therefore, it is an object of the invention to provide a method for X-ray exposure control whereby the image quality can be further enhanced, that is, notably in the case of dynamic examinations of the kind set forth.

Furthermore, it is also an object of the invention to provide an X-ray generator which includes an automatic exposure control device for carrying out such a method and in which the degree of automation is further increased and hence the image quality is no longer dependent on the skills of an operator to such a high degree.

This object is achieved in conformity with claim 1 which discloses a method of the kind set forth which includes the following steps: presetting for an exposure a maximum exposure time (Tmax) which may in principle may not be exceeded; presetting an exposure kV start voltage for an X-ray tube in dependence on an object to be examined; starting the X-ray exposure and measuring an X-ray absorption of the object; controlling the exposure by changing the exposure kV start voltage at the maximum exposure time (Tmax) when the X-ray absorption is higher than or equal to a first threshold value (B), or controlling the exposure by changing the exposure time at a constant exposure kV start voltage when the X-ray absorption is less than the first threshold value (B).

"Presetting" a maximum exposure time Tmax as well as an exposure kV start voltage is in this context is to be understood to mean presetting by an operator as well as presetting carried out, for example, by a microprocessor unit in dependence on other input data, or a fixed programming of the two variables. This also holds for all further possibilities for adjustment explained hereinafter.

In conformity with claim 4 this object is also achieved by means of an X-ray generator which is provided with an automatic exposure control unit for carrying out such a method, wherein the automatic exposure control unit includes a multiple controller for controlling an X-ray tube, which multiple controller includes with a dose controller and at least one dose rate controller which are subject to a dose rate sensor for measuring an X-ray absorption of the object.

A special advantage of these solutions resides in the fact that, notably in the case of dynamic examinations during which the absorption of the object to be examined changes, the risk of unsharp images due to an excessive exposure time is avoided. Moreover, when a suitably fast switching technology is used, the control of the exposure kV start voltage (that is, generally speaking, the organ kV voltage of an organ to be examined) can be terminated already after from approximately 1 to 2 ms, so that the exposure is then carried out with an essentially constant exposure kV voltage when the absorption remains constant during the exposure.

The dependent claims relate to advantageous further versions and embodiments of the invention.

The versions in conformity with the claims 2 and 3 enable the method to be adapted even better to given examination conditions or object properties by way of further ranges of operation.

The embodiment disclosed in claim 5 enables very fast control of the dose rate in both directions.

The embodiments disclosed in the claims 6 and 7 enable adjustment of a maximum and a minimum exposure time, respectively, for an exposure. The embodiment disclosed in claim 8 enables adjustment of a reference value for the dose or the dose power, whereas the embodiment disclosed in claim 9 enables adjustment of a start value for an exposure kV voltage whose control range as well as maximum value are adjustable.

DRAWINGS

Figure 2:
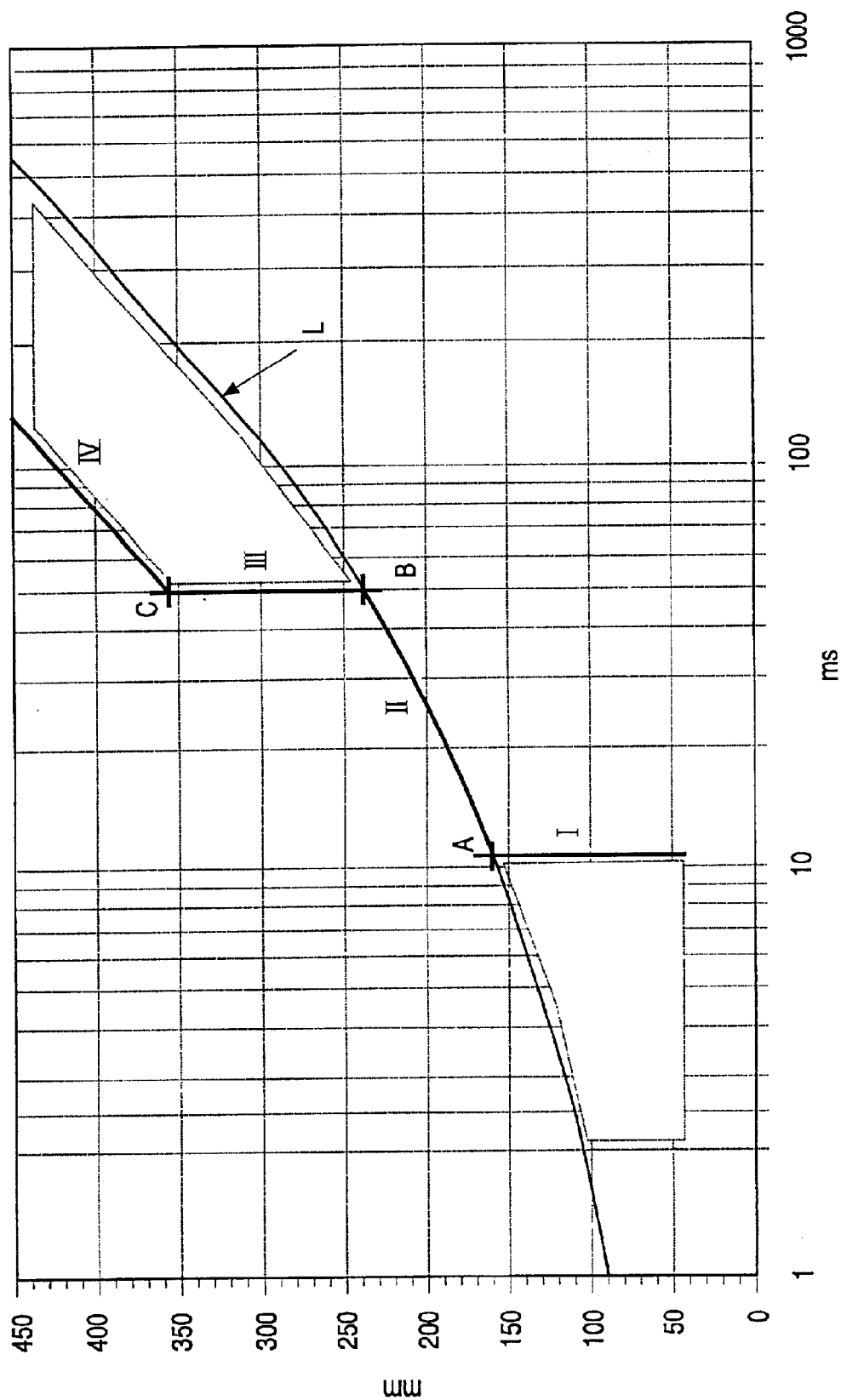

Further details, features and advantages of the invention will become apparent from the following description of a preferred embodiment which is given with reference to the drawing. Therein:

FIG. 1 shows a circuit diagram of an X-ray system provided with an X-ray generator in accordance with the invention, and FIG. 2 shows a diagram illustrating the variation in time of the exposure time in dependence on an object density.

DESCRIPTION

As is shown in FIG. 1, the essential components of an X-ray system include an X-ray tube 10 for generating X-rays which traverse a patient P and project an image of the region to be examined onto an image intensifier 11. This image is intensified in known manner so as to be converted into light signals which are bundled by a lens and diaphragm device 12, 13 so as to be picked up by a camera 14 and converted into corresponding electrical signals. These signals are applied to a usually digital image processing device 15 whereto a monitor 16 is connected so as to enable a radiologist R to observe the region of the patient P to be examined.

The X-ray tube 10 is fed by a high-voltage generator 20. The high-voltage generator 20 is connected, via a power switch 21 for switching the high voltage on and off, to a converter 22 which serves to convert a general main voltage W into a suitable input voltage for the high-voltage generator 20 and hence determines the exposure kV voltage value (being the high voltage carried by the X-ray tube).

The three previously mentioned parameters are influenced or varied by means of these components as follows.

The exposure time and the radiation dose whereto the patient is exposed can be adjusted by appropriate control of the power switch 21 by means of a first control signal. The dose rate of the X-ray tube 10 is adjusted by control of the converter 22 and hence by varying the exposure kV voltage by means of a second control signal. Moreover, the filament current for the X-ray tube 10 can be adjusted by means of a third control signal which is present at a corresponding input of the high-voltage generator 20. The three control signals mentioned are generated by a multiple controller 100 which is controlled, via a plurality of bus leads B2 to B8, by a microprocessor unit 200.

Finally, the camera 14 is provided with a beam splitter 30 in order to produce a control variable for the multiple controller 100 in the form of a dose or dose rate which occurs at the area of the camera 14 and is determined by the X-ray absorption of the patient and other image-influencing objects; the beam splitter 30 forms a sub-beam from the X-rays which is directed onto a corresponding sensor 31 (photosensor) in order to generate a dose signal or dose rate signal. The photosensor 31 is connected to a calibrator 32 which generates a voltage which is normalized to said dose or dose rate. This voltage is applied to a divider 33 whereby a reference value for the dose (for example, 0.66 $\mu$Gy) or the dose rate (for example, 66 $\mu$Gy/s) can be adjusted. To this end, the divider is connected to the microprocessor unit 200 via a first bus B1. The output signal of the divider 33 is applied to the multiple controller 100.

The multiple controller 100 includes a dose controller 110 (Amplimat) which is known per se and which receives the output signal of the divider 33, and also includes an integrator for this signal as well as a comparator. The dose controller generates the first control signal for the power switch 21 and controls the exposure time for the exposure in dependence on the dose measured on the photosensor 31 and the dose reference value adjusted via the divider 33.

There is also provided a nominal time selector 120 for a range of, for example, from approximately 4 ms to 4000 ms; this selector also receives the output signal of the divider 33 and can be controlled by the microprocessor unit 200, via the second bus B2, in order to adjust a reference value of an upper limit Tmax of an exposure time window or a maximum exposure time (for example, 50 ms).

The nominal time selector 120 is connected, via a first output, to a first dose rate controller 130 and, via a second output, to a unit 140 for generating a time window factor of, for example, between 1 and 10 (realized as an attenuator with a factor of between 1 and 0.1) whereby a reference value of a lower limit Tmin of the exposure time window or a minimum exposure time (for example, 10 ms) is formed from the selected maximum exposure time Tmax. The factor is determined in conformity with the minimum exposure time Tmin entered via the microprocessor unit 200 and the third bus B3. The output signal of the unit 140 is present at the input of a second dose rate controller 135.

The first dose rate controller 130 includes essentially a PID controller with a mean speed in the range of approximately 5 kHz and serves only for positive corrections, that is, for upwards control (increasing) of the exposure kV voltage for the X-ray tube. The second dose power controller 135 includes essentially a PID controller with a high speed in the range of approximately 10 kHz and serves exclusively for negative corrections, that is, for downwards control (decreasing) of the exposure kV voltage.

The output signals of the two dose rate controllers 130, 135 are applied to a first limiter 150; the limiter is controlled by the microprocessor unit 200, via the fourth bus B4, and serves for the adjustment of limit values whereto the exposure kV voltage may be increased or decreased at the most by the dose rate controllers (for example, by +25 kV or +15 kV or by –15 kV or –10 kV, respectively, relative to a start value).

The reference value for an exposure kV start voltage can be adjusted via the microprocessor unit and the fifth bus B5. In the case of the examination of humans, this reference value is generally the organ kV voltage of the organ to be examined (for example, 70 kV). For this purpose, the fifth bus B5 is connected to a signal mixer 160 which is connected to the output of the first limiter 150 and serves to generate the exposure kV voltage by summing its adjusted start value and the voltage values generated by the dose rate controllers.

There is also provided a second limiter 170 for the exposure kV voltage summed by the signal mixer 160; this second limiter enables, via the microprocessor unit 200 and the sixth bus B6, adjustment of a permissible overall range for this voltage of, for example, from 55 kV to 125 kV. The second limiter 170 generates, at its output, the second control signal which is ultimately applied to the converter 22 in order to convert, via this converter, the general mains voltage W in such a manner that the appropriate exposure kV voltage value can be generated by the high-voltage generator 20.

The multiple controller 100 also includes a unit 180 for generating a tube current factor in dependence on a selected image intensifier format, it being possible to input a desired current factor by way of the microprocessor unit 200, via the seventh bus B7, said factor being between, for example, 1 and 2.5.

Finally, the output of the unit 180 is connected to a unit 190 for generating a reference value for the filament current in dependence on a basic value (for example, 200 mA) which can be adjusted via the microprocessor unit and the eighth bus B8, and on the tube current factor determined by the unit 180. The output of the unit 190, generating the third control signal, is applied to the high-voltage generator 20 and controls this generator in such a manner that the reference value determined for the filament current flows through the X-ray tube 10.

Its advantageous properties become apparent notably when the X-ray system is used for dynamic examinations involving fast changes of the absorption (for example, examinations of the colon with a contrast medium). In this respect the following is to be noted: because the permissible radiation dose on the image receiver is generally specified so as to be fixed by official regulations, this dose is kept essentially constant in known exposure control systems. Consequently, in the case of a change of absorption in the object to be examined, the exposure time is varied accordingly during the acquisition of a plurality of images, that is, because of the moving contrast medium. This involves the risk that a maximum exposure time of approximately 100 ms necessary to obtain a sharp image is clearly exceeded. When the patient thicknesses are sensed in the form of water equivalent values, an exposure time range of between approximately 3.3 ms and 530 ms is adjusted by the known automatic exposure devices for a range of from 120 mm to 450 mm water equivalent values, and hence a variation by a factor of approximately 160. This factor is considered to be much too high and may lead to unsharp images.

The operation of the X-ray generator with the multiple controller (multiple stage or multiple range controller) will be described in detail hereinafter with reference to FIG. 2.

The dose rate controllers 130, 135 in the multiple controller 100 in accordance with the invention control the exposure kV values in dependence on the dose power measured by the sensor 31, essentially representing the object density (that is, the thickness of the patient), in such a manner that an adjustable exposure time range is not exceeded and notably the maximum exposure time Tmax for ensuring sharp images is not exceeded or exceeded only in the case of absorption values which are significantly higher than in known automatic exposure devices. To this end, the dose controller 110 controls in parallel, in dependence on the dose measured by the sensor 31, the dose per exposure in known manner to a value necessary for adequate exposure (an essentially constant value) by switching off the X-ray tube after the necessary exposure time t (or Tmax) has elapsed. The dose power $D_R$ required for this purpose is determined in conformity with the formula $D_R=D/t$.

In order to illustrate this operation, FIG. 2 shows the relationship between the exposure time (horizontal axis) and the object density (X-ray absorption) expressed in the water equivalent value (vertical axis); further image-influencing elements which increase the absorption also have to be added to the object density for the following explanation.

In this representation the controller operates in four different operating ranges. In a first range 1, provided for comparatively thin patients and extending below and up to a water equivalent value of approximately 160 mm (point A), the exposure time is kept constant at the minimum value Tmin which is determined by circuit-technical aspects (for example, parasitic capacitances) and amounts to approximately 11 ms in this representation, or can be adjusted via the third bus B3. In this range the exposure is adapted by a smooth variation of the exposure kV voltage by means of the second dose rate controller 135, said exposure kV voltage being reduced, starting from the start value preset via the fifth bus B5 (mean organ kV voltage) and in dependence on the object density, by up to at the most approximately −15 kV, so that the image formed with the minimum exposure time Tmin is not overexposed.

In a second range II, provided for object densities with water equivalent values of from approximately 160 mm to approximately 240 mm (between the points A and B), the exposure kV voltage remains constant at its preset start value or mean organ kV value (approximately 70 kV for the example described with reference to FIG. 1), and the exposure time t is controlled between approximately 11 ms and approximately 50 ms, in dependence on the object density (water equivalent value), by the dose controller 110.

A subsequent third range III is provided for object densities with water equivalent values of from approximately 240 mm to approximately 360 mm (between the points B and C). In this range the exposure time t remains constant at the preset maximum value Tmax (in this case approximately 50 ms) and the exposure kV voltage is smoothly increased, starting from the preset start value and in dependence on the object density (water equivalent value) up to at the most approximately 25 kV by the first dose rate controller 130, so that adequate exposure is achieved with the maximum exposure time Tmax ($D_R=D/Tmax$).

Finally, a fourth range IV (above the point C) is provided for object densities with water equivalent values of from approximately 360 mm to approximately 450 mm. In this range the exposure kV voltage remains constant at its maximum value which is determined by the second limiter 170 and which results from the sum of the preset start value and the maximum increase of approximately 25 kV. The exposure is increased from approximately 50 ms to at the most approximately 150 ms by the dose controller 110 by a smooth prolongation of the exposure time t. Even though in this example this maximum exposure time is higher than the previously mentioned maximum value for sharp images (approximately 100 ms), this value is still acceptable from a medical point of view as a compromise in respect of object density and motional unsharpness, since it is obtained exclusively for thick patients.

At the beginning of each exposure one of the dose rate controllers is activated (if necessary), in dependence on the control variable applied to the multiple controller 100, that is, the voltage (control voltage) generated by means of the sensor 31, the calibrator 32 and the divider 33, and on the adjusted maximum and minimum exposure time Tmax and Tmin, respectively.

The nominal time selector 120 and the time window factor unit 140 are provided for this purpose. Furthermore, a respective reference value of, for example, 1.0 volt is associated with the two dose rate controllers 130, 135, the second dose rate controller 135 having an effective reference value of, for example 5.0 volts (formed in conformity with the formula: reference value/attenuation factor=effective reference value) because of the attenuation factor realized by the time window factor unit 140.

In the nominal time selector 120 the control voltage is weighted, that is, subjected to a corresponding factor, in dependence on the adjustment of the maximum exposure time Tmax as carried out via the second bus B2.

When this weighted control voltage is lower than or equal to the first reference value (corresponding to a high absorption and/or a small Tmax) at the beginning of the exposure, the first dose rate controller 130 is activated so as to increase the exposure kV voltage in the described manner (range III).

Furthermore, in the unit 140 the weighted control voltage supplied by the nominal time selector 120 is subjected to a corresponding time window factor in dependence on the adjustment of the minimum exposure time Tmin as carried out via the third bus B3.

When this weighted control voltage, subjected to the time window factor, is higher than or equal to the second reference value (low absorption and/or large Tmin), the second dose rate controller 135 is activated and so as to reduce the exposure kV voltage in the described manner (range I).

When the control voltages are between the reference values, the exposure kV voltage invariably maintains its start value and the exposure control is carried out exclusively by the dose controller 110 (range II).

For the range of the water equivalent values from 120 mm to 450 mm, therefore, the multiple controller in accordance with the invention offers an exposure time range of from 11 ms to 150 ms; this corresponds to a variation by a factor of only 13.6. Furthermore, it appears that the value of the maximum exposure time of 100 ms, as required, for example, for colon examinations, is exceeded only for a water equivalent value of approximately 420, whereas this would be the case already for a water equivalent value of approximately 290 mm in the absence of the multiple controller in accordance with the invention (or in the case of control by means of the dose controller 110 only) as illustrated by the (thin) line L which is also shown in FIG. 2.

When the same values are chosen for Tmax and Tmin, the exposure at this constant value will be controlled exclusively via a variation of the exposure kV voltage.

Preferably, three different ranges II can be selected by way of adjustment of Tmax and Tmin; these ranges lie, for example, between 5 ms and 25 ms (for children) and between 10 ms and 50 ms (as shown) as well as between 20 ms and 100 ms (for adults).

Independently of these ranges, the dose selected in dependence on the desired image quality (signal-to-noise ratio), official regulations, the allowable load for the patient and/or the image intensifier format by the operator is selected via the microprocessor unit and the first bus B1. When the image intensifier format is switched over, the dose factor is transferred to the tube current (exposure current) so that the selected exposure kV voltage is maintained. In the case of image intensifier formats of, for example, 38/25/17 cm, the tube current is increased, for example, by the factors of 1/1.6/2.5. The described units 180 and 190 are used for this purpose.

The control of the exposure kV voltage between a minimum value and a maximum value in the ranges I and III can be adjusted via the microprocessor unit 200 and the fourth bus B4. Preferably, there are provided two voltage ranges which lie, for example, between −15 kV and +25 kV (as shown) or between −10 kV and +15 kV relative to the exposure kV start voltage (mean organ kV voltage).

For this example the first dose rate controller 130 (positive controller) is arranged to increase the exposure kV start voltage in the range III by a maximum of +15 kV or +25 kV, whereas the second dose rate controller 135 (negative controller) serves to reduce the exposure kV start voltage in the range I by a maximum of −10 kV or −15 kV. Because a separate controller is used for each direction, and because an as fast as possible (notably analog) switching technique is appropriately chosen, a correspondingly fast increase and reduction of the exposure kV voltage (and hence of the X-ray dose rate) are possible, so that the control of the exposure kV voltage is terminated approximately from 1 ms to 2 ms after the start of the exposure, after which the exposure kV voltage remains essentially constant until the termination of the exposure by the dose controller 110.

Summarizing it can be said that the multiple controller in accordance with the invention enables control of the dose rate $D_R$ of the X-ray tube in dependence on the object density (patient thickness) in such a manner that the dose controller does not have to leave a time window defined by the range II, or has to leave it only in the case of an essentially higher object density (point C), so that optimum image sharpness is ensured also in the case of dynamic exposures. The exposure time t is then controlled in conformity with the formula $t=D/D_R$ (ranges II and IV), that is, independently and without reactive effects from the dose D adjusted by the operator. In the ranges I and III, in which the exposure time is constant at Tmin and Tmax, respectively, the exposure kV voltage is adjusted in conformity with the formula $D_R=D/t$ within from 1 ms to 2 ms after the start of the exposure, after which it remains essentially constant until the end of the exposure (switching off of the exposure by the dose controller 110).

For the sake of clarity it is to be noted that the detected X-ray absorption of the "object" always includes also the absorption by other elements which are present in the beam path between the X-ray tube and the sensor 31 which is arranged directly on the pick-up device (camera 14). It is thus ensured that the exposure is optimum while taking into account the object to be examined and all image-influencing elements (such as the image intensifier 11, the lens 12 etc.).

The described control concept is advantageous in particular in the case of formation of a number of images in rapid succession, because in that case adjustment of a correspondingly small maximum exposure time Tmax ("time priority") can prevent the exposure time from becoming longer than the time available for a single image.

A further, essential advantage of the multiple controller resides in the fact that it can be very universally used. This is due mainly to the fact that all relevant data for the exposure, for example, the exposure kV start voltage which is chosen in dependence on the organ to be examined, the exposure time window, the control ranges of the exposure kV voltage etc., are controlled via a microprocessor unit.

Furthermore, the controller can be used independently from the selected image receiver and can be used in conjunction with the known image intensifier video cameras as well as with the novel digital flat detectors (FDXD) or storage foils (PCR). The dose rate signal is obtained in the first case (indirect technique) by means of a photosensor with a fast signal response time (<100 $\mu$s) while in the case of the direct techniques (FDXD, PCR) it is acquired with a fast signal response time (<100 $\mu$s) by means of an ionization chamber with an output for the dose rate signal; a calibration to absolute dose values ($\mu$Gy) or absolute dose rate values ($\mu$Gy/s) is then preferably performed at a reference voltage of 1.0 V.

The control of the controller strategy can be programmed in an EPX database structure.

The multiple controller can be used both for an exposure for the formation of a single image as well as for an exposure for the formation of the images of an image sequence (moving images) during which the absorption of the object changes.

Moreover, the multiple controller can be used for all medical techniques such as, for example, tomography, digital direct imaging (DSI), digital exposure techniques such as cine techniques as well as a conventional film foil technique etc. and also for other X-ray systems.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A method for X-ray exposure control, notably for exposures carried out during dynamic X-ray examinations of an object comprising the steps of:

presetting for an exposure a maximum exposure time which may in principle not be exceeded;

presetting an exposure kV start voltage for an X-ray tube in dependence on an object to be examined;

starting the X-ray exposure and measuring an X-ray absorption of the object;

controlling the exposure by changing at least one of: a) the exposure kV start voltage at the maximum exposure time when the X-ray absorption is higher than or equal to a first threshold value; and b) the exposure time at a constant exposure kV start voltage when the X-ray absorption is less than the first threshold value.

2. A method as claimed in claim 1, wherein a minimum exposure time is preset for an exposure, the exposure taking place by changing at least one of: a) the exposure kV start voltage at the minimum exposure time when the X-ray absorption is less than or equal to a second threshold value; and b) the exposure taking place by changing the exposure time with a constant exposure kV start voltage when the X-ray absorption exceeds the second threshold value.

3. A method as claimed in claim 1, wherein the exposure kV voltage is increased only to a predetermined maximum value and an increase of the exposure beyond this maximum value is performed by prolonging the exposure time at the maximum exposure kV voltage.

4. An X-ray generator comprising:

an automatic exposure control unit, said automatic exposure control unit including a multiple controller for controlling an X-ray tube, which multiple controller includes a dose controller and at least one dose rate controller which are subject to a dose rate sensor for measuring an X-ray absorption of the object, whereby X-ray exposure is changed by changing at least one of: a) an exposure kV start voltage at a maximum exposure time when the X-ray absorption is higher than or equal to a first threshold value; and b) an exposure time at a constant exposure kV start voltage when the X-ray absorption is less than the first threshold value.

5. An X-ray generator as claimed in claim 4 further comprising:

a first dose rate controller for increasing the dose rate of the X-ray tube; and a second dose rate controller for reducing the dose rate of the X-ray tube, said dose rate controllers being connected in parallel.

6. An X-ray generator as claimed in claim 5 further comprising:

a first time unit whereby a maximum exposure time can be preset for an exposure and which is connected between the dose rate sensor and the first and second dose rate controllers so as to act on said dose rate controllers.

7. An X-ray generator as claimed in claim 6 further comprising:

a second time unit whereby a minimum exposure time can be preset for an exposure and which is connected between the first time unit and the second dose rate controller so as to act thereon.

8. An X-ray generator as claimed in claim 4 wherein the dose rate sensor is operatively connected, via a calibrator and a divider for adjusting a reference value of the dose or the dose rate, to the dose controller and the at least one of the dose rate controllers.

9. An X-ray generator as claimed in claim 4 further comprising:

a third controller which is subject to the at least one dose rate controller in order to adjust a start value of an exposure kV voltage for an X-ray tube as well as to adjust the control range and the maximum value thereof.

10. An X-ray generator as claimed in claim 4 further comprising:

a fourth controller for generating a filament current for the X-ray tube in dependence on a basic value as well as for forming a tube current factor which is adjustable in dependence on an image intensifier format.

11. An X-ray generator as claimed in claim 10 further comprising:

a microprocessor unit whereby the divider as well as the first through fourth controllers are adjusted via a plurality of bus leads.

* * * * *